US005700452A

United States Patent [19]
Deckner et al.

[11] Patent Number: 5,700,452
[45] Date of Patent: Dec. 23, 1997

[54] COMPOSITIONS FOR IMPARTING AN ARTIFICIAL TAN AND PROTECTING THE SKIN FROM ULTRA-VIOLET RADIATION

[75] Inventors: George Endel Deckner; Francisco Antonio Pichardo; Noelle Carolyn Alban, all of Cincinnati; Marsha Carolyn Sills, Fairborn, all of Ohio

[73] Assignee: The Procter & Gamble Company, Cincinnati, Ohio

[21] Appl. No.: 576,267

[22] Filed: Dec. 21, 1995

Related U.S. Application Data

[63] Continuation of Ser. No. 371,060, Jan. 10, 1995, abandoned, which is a continuation of Ser. No. 73,276, Apr. 16, 1993, abandoned.

[51] Int. Cl.$^6$ .................. A61K 7/40; A61K 7/42; A61K 7/44; A61K 7/00
[52] U.S. Cl. .................. 424/59; 424/60; 424/400; 424/401
[58] Field of Search .................. 424/59, 60

[56] References Cited

U.S. PATENT DOCUMENTS

| | | | |
|---|---|---|---|
| 2,949,403 | 8/1960 | Andreadis et al. | 424/60 |
| 3,177,120 | 4/1965 | Black et al. | 167/90 |
| 3,184,388 | 5/1965 | Kalopissis | 167/90 |
| 3,272,713 | 9/1966 | Runge | 167/90 |
| 3,529,055 | 9/1970 | Skoultchi et al. | 424/59 |
| 3,755,560 | 8/1973 | Dickert et al. | 424/59 |
| 3,920,808 | 11/1975 | Fusaro | 424/59 |
| 4,419,343 | 12/1983 | Pauly | 424/59 |
| 4,434,154 | 2/1984 | McShane | 424/60 |
| 4,599,379 | 7/1986 | Flesher et al. | 524/801 |
| 4,628,078 | 12/1986 | Glover et al. | 526/303.1 |
| 4,673,704 | 6/1987 | Flesher et al. | 524/519 |
| 4,806,345 | 2/1989 | Bhattacharyya | 424/70 |
| 4,832,943 | 5/1989 | Grollier et al. | 424/59 |
| 4,835,206 | 5/1989 | Farrar et al. | 524/457 |
| 4,849,484 | 7/1989 | Heard | 525/221 |
| 4,868,163 | 9/1989 | Takei et al. | 514/76 |
| 4,939,179 | 7/1990 | Cheney et al. | 514/789 |
| 5,100,660 | 3/1992 | Hawe et al. | 424/78.35 |
| 5,221,530 | 6/1993 | Janchitraponvej et al. | 424/70 |
| 5,229,107 | 7/1993 | Sabatelli et al. | 424/47 |
| 5,232,688 | 8/1993 | Ziegler et al. | 424/59 |

FOREIGN PATENT DOCUMENTS

| | | | |
|---|---|---|---|
| 131591 | 3/1967 | Czechoslovakia | A61K 7/42 |
| 227012 | 7/1987 | European Pat. Off. | A61K 7/00 |
| 228868 | 7/1987 | European Pat. Off. | C08F 226/02 |
| 456545 | 4/1991 | European Pat. Off. | A61K 7/42 |
| 425324 | 5/1991 | European Pat. Off. | A61K 7/02 |
| 547864 | 6/1993 | European Pat. Off. | A61K 7/42 |
| 506622 | 10/1982 | Spain | A61K 7/42 |
| WO 92/17159 | 10/1992 | WIPO | A61K 7/42 |
| WO 93/07903 | 4/1993 | WIPO | A61K 47/32 |

OTHER PUBLICATIONS

M. S. Balsam et al., (ed.) "Cosmetic Science and Technology" 2nd edition, Dec. 10, 1973, vol. 1, ppl. 293–305, Wiley–Interscience, New York.

Primary Examiner—Shelley A. Dodson
Attorney, Agent, or Firm—Darryl C. Little; David K. Dabbiere; Jacobus C. Rasser

[57] ABSTRACT

The present invention relates to emulsion compositions which are useful for imparting both an artificial tan to human skin and for providing protection to the skin from the harmful effects of UV radiation. These compositions have good stability at acidic pH values, are highly substantive to the skin, and provide a natural looking tan.

22 Claims, No Drawings

COMPOSITIONS FOR IMPARTING AN ARTIFICIAL TAN AND PROTECTING THE SKIN FROM ULTRA-VIOLET RADIATION

This is a continuation of application Ser. No. 08/371,060, filed on Jan. 10, 1995, which is a continuation of application Ser. No. 08/073,276, filed on Apr. 16, 1993 both abandoned.

TECHNICAL FIELD

The present invention relates to oil-in-water emulsion compositions having improved stability at acidic pH values. These compositions are useful for imparting an artificial tan to human skin and for protecting the skin from the harmful effects of UV radiation. These emulsions comprise an artificial tanning active, a sunscreen agent, a cationic emulsifier, and a thickener. In further embodiments, these compositions also comprise a polymeric stabilizing agent. The present invention also relates to methods for preparing these compositions, methods for providing an artificial tan to human skin, and methods for protecting human skin from the harmful effects of ultraviolet radiation.

BACKGROUND OF THE INVENTION

A sun-tanned appearance is a symbol of a healthy, dynamic, and active life. Yet, the damaging effects of sunlight and artificial sources of ultraviolet radiation on the skin are well documented. These effects are cumulative and potentially serious, and include sunburn, skin cancer, and premature aging of the skin. These effects associated with exposure to ultraviolet radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 3, pp. 15–24 (1982); and U.S. Pat. No. 4,387,089, DePolo, issued Jun. 7, 1983; the disclosures of all of which are incorporated herein by reference.

Sunscreens are the most common agents used for sun protection. However, sunscreens also have the disadvantage of preventing or greatly diminishing the tanning response. Thus, if an individual uses a sunscreen for protection from ultraviolet radiation, he or she does so at the expense of foregoing a tanned appearance. Furthermore, even if an individual is willing to accept the risks associated with exposure to ultraviolet radiation to obtain a tan, there are situations in which it may not be practical or even possible to do so because of time constraints, weather conditions, etc. Therefore, it would be highly desirable to develop products for providing protection from the harmful effects of ultraviolet radiation, and yet at the same time which deliver a tanned appearance to the skin, whenever desired without the need for exposure to ultraviolet radiation.

It is generally known that dihydroxyacetone, when applied topically to human skin, will produce a tanned appearance, i.e. an artificial tan. U.S. Pat. No. 4,708,865, to Turner, issued Nov. 24, 1987 describes the use of hydroalcoholic solutions of dihydroxyacetone for tanning the skin; U.S. Pat. No. 4,466,805, to Welters, issued Aug. 21, 1984 describes hair and skin coloring formulations containing dihydroxyacetone; and U.S. Pat. No. 2,949,403, to Andreadis et al., issued Aug. 16, 1960 describes artificial tanning formulations containing dihydroxyacetone in an oleaginous base. However, it is also known that emulsion products containing dihydroxyacetone have a short shelf life, tending to darken and develop disagreeable off-odors over time, with a concomitant loss of emulsion integrity. Dihydroxyacetone is known to be more stable at acidic pH values. See "Dihydroxyacetone for Cosmetics", E. Merck Technical Bulletin, 03–304 110, 319 897, 180 588. However, many commonly used thickening agents and emulsifiers (e.g. carbomers, gums, and anionic and amphoteric emulsifiers) are not compatible with acidic compositions.

Dihydroxyacetone is also relatively sensitive to heat, light, and moisture. Dihydroxyacetone can react with other ingredients in a formulation, especially with nitrogen-containing compounds, such as amines, amino acids, and the like. In fact, without being limited by theory, dihydroxyacetone is believed to provide an artificial tan to human skin by its reaction with the nitrogen containing proteins of the skin. See L. Goldman et al., "Investigative Studies with the Skin Coloring Agents Dihydroxyacetone and Glyoxal", *The Journal of Investigative Dermatology*, vol. 35, pp. 161–164 (1960); and E. Wittgenstein et al., "Reaction of Dihydroxyacetone (DHA) with Human Skin Callus and Amino Compounds", *The Journal of Investigative Dermatology*, vol. 36, pp. 283–286 (1961). This incompatibility of dihydroxyacetone with nitrogen containing compounds has limited the scope of artificial tanning products in the past. However, in the present invention, it has been found that dihydroxyacetone is highly compatibile with the nitrogen-containing cationic polymers and cationic emulsifiers used herein.

Most currently available artificial tanning products have the disadvantage of not providing the desired control over color development of the tan. Artificial tans are often either too light or too dark, and tend to be too orange, uneven, or unnatural in appearance. Furthermore, artificial tans tend to take too long to develop, and once obtained, tend to fade too quickly and unevenly. Therefore, it would be highly desirable to provide dihydroxyacetone containing products which are chemically and physically stable, especially at acidic pH values, which are aesthetically pleasing, and which overcome these color development limitations.

Most topical tanning and sunscreen compositions have the disadvantage of being removed too easily from the skin by water, perspiration, and rub-off. In other words, such products are not as substantivie to the skin as would be desired. Therefore, the need exists for products which provide a tanned appearance and sunprotection, and which are truly substantive to the skin.

It is therefore an object of the present invention to provide oil-in-water emulsion compositions for imparting a natural looking artificial tan to human skin and to provide protection from the harmful effects of UV radiation.

It is another object of the present invention to provide such compositions which exhibit a high degree of chemical and physical stability, especially at acidic pH values.

It is another object of the present invention to provide such compositions which are highly substantive to the skin and are resistant to water, perspiration, and rub-off.

It is another object of the present invention to provide such compositions which are aesthetically appealing.

It is another object of the present invention to provide a method for artificially tanning human skin and for providing protection from ultraviolet radiation.

These and other objects of this invention will become apparent in light of the following disclosure.

SUMMARY OF THE INVENTION

The present invention relates to an oil-in-water emulsion composition useful for providing an artificial tan and UV protection comprising:

(a) from about 0.1% to about 20% dihydroxyacetone;
(b) from about 0.1% to about 30% of a sunscreen agent;
(c) from about 0.1% to about 10.0% of a crosslinked cationic polymer of the formula: $(A)_l(B)_m(C)_n$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is acrylamide, l is an integer of 0 or greater, m is an integer of 1 or greater, and n is an integer of 0 or greater, wherein said polymer contains a crosslinking agent;
(d) from about 0.1% to about 10% of a cationic emulsifier; and
(e) from about 30% to about 99.6% water;

wherein said composition has a pH from about 2.5 to about 7.

All percentages and ratios used herein are by weight of the total composition and all measurements made are at 25° C., unless otherwise designated. The invention hereof can comprise, consist of, or consist essentially of, the essential as well as optional ingredients and components described herein.

DETAILED DESCRIPTION OF THE INVENTION

The compositions of the present invention are useful for providing an artificial tan and for protecting the skin from the harmful effects of ultraviolet radiation. These compositions have good chemical and physical stability in the acidic pH range. These compositions are also highly substantive to the skin, being resistant to water, perspiration, and rub-off.

Emulsion Compositions

The compositions of the present invention are in the form of emulsion compositions, preferably oil-in-water emulsions, whereby the oil phase and the water phase can contain ingredients well known in the art. These types of emulsions are preferred because of their desirable aesthetic properties and their utility as vehicles for the dihydroxyacetone and the other essential and optional components of this invention. These emulsions can span a broad range of consistencies from thin lotions to heavy creams. These emulsions can have viscosities ranging from about 100 cps to about 200,000 cps. These emulsion can comprise the essential and optional components described herein.

pH Requirements

The pH of a formulation containing dihydroxyacetone is an important factor in determining both the chemical and physical stability of the composition. For example, it is well known that dihydroxyacetone rapidly degrades at extremes of alkaline pH. Also, emulsion compositions containing dihydroxyacetone tend to loose viscosity and suffer emulsion breakdown over time.

The compositions of the present invention preferably have a pH range from about 2.5 to about 7, more preferably from about 2.5 to about 6, and most preferably from about 3.5 to about 5. It has been found that a buffer system is not required for achieving the stable emulsion compositions described herein.

Dihydroxyacetone

The emulsion compositions of the present invention comprise from about 0.1% to about 20%, more preferably from about 2% to about 7%, and most preferably from about 3% to about 5% of dihydroxyacetone.

Dihydroxyacetone, which is also known as DHA or 1,3-dihydroxy-2-propanone, is a white to off-white, crystalline powder having a characteristic sweet, cooling taste. The compound can exist as a mixture of monomers and dimers, with the dimer predominating. Heating or melting dimeric dihydroxyacetone converts the material into the monomeric form. The conversion of the dimer to the monomer also takes place in aqueous solution. See *The Merck Index*, Tenth Edition, entry 3167, p. 463 (1983), and "Dihydroxyacetone for Cosmetics", E. Merck Technical Bulletin, 03–304 110, 319 897, 180 588; both of these references being incorporated herein by reference in their entirety.

Without being limited by theory, it is believed that dihydroxyacetone reacts with the amino acids and amino groups of the skin keratin forming the brown colored compounds which provide an artificial tan. The process takes place in the outer layers of the epidermis. It is believed that the monomer is the active form responsible for this phenomenon. There is much evidence to suggest that the reaction of dihydroxyacetone with the components of the skin is similar to the Maillard Reaction. In this reaction, reducing sugars react with amino acids, proteins, and peptides to form various adducts which are ultimately converted into brown-colored compounds. See V. R. Usdin, Artificial Tanning Preparations, *Cosmetics and Toiletries*, vol. 91 pp. 29–32 (March 1976), this reference being incorporated herein by reference in its entirety. Dihydroxyacetone is commercially available from E. Merck (Darmstadt, Germany) and Gist-Brocades Food Ingredients, Inc. (King of Prussia, Pa).

Cationic Water-Soluble Polymers

The compositions of the present invention comprise from about 0.1% to about 10%, more preferably from about 0.1% to about 5%, and most preferably from about 0.5% to about 2% of a crosslinked cationic polymer.

The cationic polymers of this type are generally described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

These polymers are high molecular weight materials containing cationic, usually quaternized, nitrogen moieties. These polymers can be characterized by the general formula: $(A)_l(B)_m(C)_n$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer having one carbon-carbon double bond, l is an integer of 0 or greater, m is an integer of 1 or greater, and n is an integer of 0 or greater. The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide.

These $(A)_l(B)_m(C)_n$ polymers can also contain a crosslinking agent, which is most typically a material containing two or more unsaturated functional groups. In other words, these polymers are expressly intended to also include the crosslinking agent in addition to the (A), (B), and (C) monomer units. As is well known to one of ordinary skill in polymer science, a crosslinking agent reacts with the monomer units of a polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

When the crosslinking agent is present, widely varying amounts of it can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about about 500 ppm of the total weight of the polymer on a weight/weight basis.

The polymerization is preferably conducted under known conditions such that the polymers are water soluble and have a high molecular weight, generally about 1 million, for instance up to 30 million. The intrinsic viscosity, measured in molar sodium chloride solution at 25° C., is generally above 6, for instance from 8 to 14.

These cationic polymers can be made by polymerization of a solution containing from about 20% to about 60%, generally from about 25% to about 40%, by weight monomer, in the presence of an initiator (usually redox or thermal) until the polymerization terminates. When the polymer is to be crosslinked, a suitable amount of the crosslinking agent is also added to the solution of the monomers to be polymerized to incorporate the crosslinking agent into the polymer. In the polymerization reactions, the temperature generally starts low, e.g. 0° to 95° C. The polymerization can be conducted by forming a reverse phase dispersion of an aqueous phase of the monomers (and also any additional crosslinking agents) into a nonaqueous liquid, e.g. mineral oil and the like.

All percentages describing the polymer herein are molar, unless otherwise specified. When the polymer contains acrylamide, the molar proportion of acrylamide, based on the total molar amount of acrylamide, dialkylaminoalkyl acrylate and dialkylaminoalkyl methacrylate, is generally from about 20% to about 99%, more preferably from about 50% to about 90%.

Where monomer A is present, the ratio of monomer A:monomer B used in this process, and thus the ratio of groups A and B in the final polymer, on a molar basis is preferably about 99:5 to about 15:85, more preferably from about 80:20 to about 20:80.

Alternatively, in one class of processes, the ratio is about 5:95 to 50:50, i.e., the cationic monomer is mainly methacrylate. In these processes, the ratio is generally being achieved in the range of from about 5:95 to about 25:75.

In another alternative class of processes, the ratio A:B is from about 50:50 to about 85:15, the cationic monomers being mainly acrylate. Preferably the ratio A:B is about 60:40 to 85:15, most preferably about 75:25 to 85:15.

Preferred is where monomer A is not present and the ratio of monomer B:monomer C is from about 30:70 to about 70:30, preferably from about 40:60 to about 60:40 and most preferably from about 45:55 to about 55:45.

A class of cationic polymers useful herein is one conforming to the general structure $(A)_l(B)_m(C)_n$ wherein l is zero, (B) is methyl quaternized dimethylaminoethyl methacrylate, the ratio of (B):(C) is about 45:55 to about 55:45, and the optional crosslinking agent is methylenebisacrylamide. An example of such a cationic polymer is one that is commercially available as a mineral oil dispersion (which can also include various dispersing aids such as PPG-1 trideceth-6) under the trademark Salcare$^R$ SC92 from Allied Colloids Ltd. (Norfolk, Va.). This polymer has the proposed CTFA designation, "Polyquaternium 32 (and) Mineral Oil".

Another class of cationic polymers useful herein is one that does not contain the acrylamide monomer, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate copolymers and homopolymers preferably contain a crosslinking agent as described above.

A cationic homopolymer useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mineral oil dispersion also containing PPG-1 trideceth-6 as a dispersing aid, from Allied Colloids Ltd, (Norfolk, Va.) under the trademark Salcare$^R$ SC95. This polymer has recently been given the CTFA designation "Polyquaternium 37 (and) Mineral Oil (and) PPG-1 Trideceth-6".

Sunscreen Agent

The compositions of the present invention comprise from about 0.1% to about 30%, more preferably from about 0.5% to about 25%, and most preferably from about 1% to about 20% of at least one sunscreen agent. Exact amounts of sunscreen agent will vary depending upon the sunscreen or sunscreens chosen and the desired Sun Protection Factor (SPF) to be achieved. SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See *Federal Register*, Vol. 43, No. 166, pp. 38206–38269, Aug. 25, 1978, which is incorporated herein by reference in its entirety.

A wide variety of sunscreen agents are useful herein. These sunscreen agents include both organic compounds and their salts as well as inorganic particulate materials. Without being limited by theory, it is believed that sunscreen agents provide protection from ultraviolet radiation by one or more of the following mechanisms including absoprtion, scattering, and reflection of the ultraviolet radiation. Non-limiting examples of these sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991;, U.S. Pat. No. 5,160,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20, 1991; U.S. Pat. No. 4,999,186, to Sabatelli et al., issued Mar. 12, 1991; U.S. Pat. No. 4,937,370, to Sabatelli, issued Jun. 26, 1990; and Segarin, et al., at Chapter VIII, pages 189 et seq., of *Cosmetics Science and Technology*; all of these documents being incorporated herein by reference in their entirety.

Preferred among the sunscreen agents are those selected from the group consisting of 2-ethyl hexyl p-methoxycinnamate, octyl salicylate, octocrylene, oxybenzone, 2-ethylhexyl N,N-dimethylaminobenzoate, p-aminobenzoic acid, 2-phenyl-benzimidazole-5-sulfonic acid, homomenthyl salicylate, DEA p-methoxycinnamate, 4,4'-methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy) benzophenone, 4-N,N-dimethylaminobenzoic acid ester with 4-hydroxydibenzoylmethane, 4-N,N-dimethylaminobenzoic acid ester with 4-(2-hydroxyethoxy) dibenzoylmethane, 4-N,N-di(2-ethylhexyl)aminobenzoic acid ester with 2,4-dihydroxybenzophenone, 4-N,N-di(2-ethylhexyl)aminobenzoic acid ester with 2-hydroxy-4-(2-hydroxyethoxy)benzophenone, 4-N,N-di(2-ethylhexyl) aminobenzoic acid ester with 4-hydroxydibenzoylmethane, 4-N,N-di(2-ethylhexyl)aminobenzoic acid ester with 4-(2-hydroxyethoxy)dibenzoylmethane, 4-N,N-(2-ethylhexyl) methylaminobenzoic acid ester with 2,4-dihydroxybenzophenone, 4-N,N-(2-ethylhexyl) methylaminobenzoic acid ester with 2-hydroxy-4-(2-hydroxyethoxy)benzophenone, 4-N,N-(2-ethylhexyl) methylaminobenzoic acid ester with 4-hydroxydibenzoylmethane, 4-N,N-(2-ethylhexyl) methylaminobenzoic acid ester with 4-(2-hydroxyethoxy) dibenzoylmethane, titanium dioxide, zinc oxide, iron oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, titanium dioxide, zinc oxide, iron oxide, and mixtures thereof.

Most preferred for use in the compositions described herein are the sunscreen agents selected from the group consisting of ethylhexyl p-methoxycinnamate, octocrylene, octyl salicylate, oxybenzone, 2-phenylbenzimidazole-5-sulfonic acid, 4,4'-methoxy-t-buyl-methoxydibenzoylmethane, 3-(4-methylbenzylidene) camphor, 3-benzylidene camphor, titanium dixoide, zinc oxide, iron oxide, and mixtures thereof.

Cationic Emulsifier

The compositions of the present invention comprise from about 0.1% to about 10%, more preferably from about 0.1% to about 2%, and most preferably from about 0.1% to about 1% of a cationic emulsifier. The purpose of this material is to emulsify the oil and water phase ingredients. Even though the term "emulsifier" is used herein, this term is also intended to encompass the term "surfactant", which can be used interchangeably.

A wide variety of cationic emulsifiers and surfactants useful herein are disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120, 532, to Wells et al., issued Jun. 9, 1992; U.S. Pat. No. 4,387,090, to Bolich, issued Jun. 7, 1983;; U.S. Pat. No. 3,155,591, Hilfer, issued Nov. 3, 1964; U.S. Pat. No. 3,929, 678, to Laughlin et al., issued Dec. 30, 1975; U.S. Pat. No. 3,959,461, to Bailey et al., issued May 25, 1976; *McCutcheon's, Detergents & Emulsifiers*, (North American edition 1979) M. C. Publishing Co.; and Schwartz, et al., *Surface Active Agents, Their Chemistry and Technology*, New York: Interscience Publishers, 1949; all of these documents being incorporated herein by reference in their entirety.

The cationic emulsifiers useful herein include quaternary ammonium salts such as those having the formula:

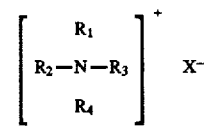

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants can include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a cocunt fatty acid, which generally have mixtures of alkyl chains in the C12 to C14 range. Examples of quaternary ammonium salts derived from these tallow and cococut sources include ditallow dimethyl ammonium chlroide, ditallow dimehtyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred cationic emulsifiers are those selected from the group consisting of dilauryl dimethyl ammoniun chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic emulsifiers are those selected from the group consisting of dilauryl dimethyl ammoniun chloride, distearyl dimethyl ammonium chloride, dimyristyl dimethyl ammonium chloride, dipalmityl dimethyl ammonium chloride, distearyl dimethyl ammonium chloride, and mixtures thereof.

Water

The emulsions of the present invention comprise from about 30% to about 99.6%, more preferably from about 50% to about 90%, and most preferably from about 60% to about 80% water.

Optional Components

Each of the water and oil phases of the emulsions can comprise a wide variety of optional components. Typical of such optional components are:

Fatty Alcohol

An optional component of the present invention is a fatty alcohol. These fatty alochols can be used to increase emulsion viscosity and to provide a smooth feel to the finished emulsion. When used herein, these fatty alcohols can comprise from about 0.1% to about 10%, more preferably from about 0.1% to about 7.5%, and most preferably from about 0.1% to about 5% of the compositions.

By the term "fatty alcohol" is meant any organic alcohol from natural or synthetic sources having from about 10 to about 40 carbon atoms, more preferably from about 10 to about 30 carbon atoms, and most preferably from about 12 to about 22 carbon atoms.

Nonlimiting examples of fatty alcohols include those selected from the group consisting of lauryl alcohol, myristyl alcohol, palmityl alcohol, stearyl alcohol, isostearyl alcohol, oleyl alcohol, linoleyl alcohol, linolenyl alcohol, ricinoleyl alcohol, behenyl alcohol, and mixtures thereof. Examples of fatty alcohols are described in CTFA International Cosmetic Ingredient Dictionary Fourth Edition, which is incorporated herein by reference in its entirety.

Humectants

Another optional component of the compositions of the present invention is a humectant. When used herein, the humectant can comprise from about 0.1% to about 20%, more preferably from about 0.5% to about 10%, and most preferably from about 1% to about 5% of the compositions. Even though these materials are defined herein as humectants, they can also possess moisturizing, skin conditioning, and other related properties.

Examples of humectants useful herein include materials such as urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol, and the like; polyethylene glycol; sugars and starches; sugar and starch derivatives (e.g., alkoxylated glucose); hyaluronic acid; chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; propoxylated glycerol (as described in U.S. Pat. No. 4,976,953 to Orr et al., issued Dec. 11, 1990, which is incorporated by reference herein in its entirety); and mixtures thereof.

Preferred humectants useful in the compositions of the present invention are the C3–C6 diols and triols. More preferred as humectants are the C3–C6 diols and triols selected from the group consisting of propylene glycol, 1,3-dihydroxypropane, glycerin, butylene glycol, hexylene glycol, 1,4-dihydroxyhexane, 1,2,6-hexanetriol, and mixtures thereof. Most preferred as humectants are those selected from the group consisting of glycerin, butylene glycol, hexylene glycol, and mixtures thereof. Among these humectants, glycerin is especially preferred.

Emollients

The compositions of the present invention can also include an emollient. Examples of suitable emollients include, but are not limited to, volatile and non-volatile silicone oils (e.g., dimethicone, cyclomethicone, dimethiconol, and the like), highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 0.5% to about 50%, more preferably from about 0.5% to about 25%, and most preferably from about 0.5% to about 15% by weight of the compositions of the present invention.

Additional Ingredients

A variety of additional ingredients can be incorporated into the compositions of the present invention. Non-limiting examples of these additional ingredients include vitamins and derivatives thereof (e.g. tocopherol, tocopheryl acetate, retinoic acid, retinol, retinoids, and the like); other thickening agents (e.g., polyacrylamide and $C_{13-14}$ isoparaffin and laureth-7, available as Sepigel from Seppic Corp.); resins; gums; waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220$^R$); preservatives for maintaining the antimicrobial integrity of the compositions; skin penetration aids such as DMSO, 1-dodecylazacycloheptan-2-one (available as Azone from the Upjohn Co.) and the like; anti-acne medicaments (e.g., resorcinol, salicylic acid, erythromycin, benzoyl peroxide, zinc, and the like); skin bleaching (or lightening) agents including but not limited to hydroquinone, kojic acid and sodium metabisulfite; antioxidants; chelators and sequestrants; and aesthetic components such as fragrances, pigments, colorings, essential oils, skin sensates, astringents, skin soothing agents, skin healing agents and the like. nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

Methods for Providing an Artificial Tan and for Protecting the Skin from UV Radiation To obtain an artificial tan and/or protection from the harmful effects of UV radiation, an effective amount of the emulsion of the present invention is applied to the skin. By "effective" is meant an amount sufficient to provide an artificial tan and protection from UV radiation, but not so much as to cause any side effects or skin reactions. By "protection" is meant that these compositions attenuate or reduce the amount of UV radiation reaching the skin's surface. Quantities of emulsion which are typically applied to provide an artificial tan and/or protection from the harmful effects of UV radiation are about, but not limited to, 2 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Examples I–III

Artifical Tanning Lotions Containing Sunscreens

| | % Weight | | |
|---|---|---|---|
| | I | II | III |
| Phase A | | | |
| Octyl Methoxycinnamate | 3.50 | 7.50 | 7.00 |
| Octocrylene | 1.00 | 3.75 | 7.50 |
| Benzophenone-3 | — | 2.00 | 4.20 |
| PVP Eicosene Copolymer | 1.00 | 1.00 | 1.00 |
| Glyceryl Tribehenate | 0.75 | 0.75 | 0.75 |
| Cetyl Palmitate | 0.75 | 0.75 | 0.75 |
| Polyquaternium 37 (and) Mineral Oil (and) PPG-1 Trideceth 6[1] | 1.75 | 1.50 | 1.25 |
| Isohexadecane | 1.00 | 1.00 | 2.00 |
| Cetyl Alcohol | 0.50 | 0.50 | 0.50 |
| Extracts of Aloe, Lanolin, Cocoa Butter, Palm, Chamomile, Eucalyptus, and Guava | 0.50 | — | — |
| Phase B | | | |
| Water | QS100 | QS100 | QS100 |
| Distearyl Dimethyl Ammonium Chloride | 0.20 | 0.20 | 0.20 |
| Hydroxyethylcellulose | 0.20 | 0.20 | 0.20 |
| Disodium EDTA | 0.05 | 0.05 | 0.05 |
| Phase C | | | |
| Water | 2.00 | 2.00 | 2.00 |
| Butylene Glycol | 2.00 | 2.00 | 2.00 |
| DMDM Hydantoin (and) Iodopropynyl Carbamate | 0.20 | 0.20 | 0.20 |
| Phase D | | | |
| Water | 6.00 | 6.00 | 6.00 |
| Dihydroxyacetone | 3.00 | 3.00 | 3.00 |
| Phase E | | | |
| Cyclomethicone | 2.00 | — | — |
| Phase F | | | |
| Fragrance | 1.00 | 0.50 | 0.50 |

[1] Available as Salcare$^R$ SC95 from Allied Colloids Ltd. (Norfolk, VA).

In a suitable vessel the phase A ingredients are combined and heated with mixing to 80°–85° C. to form an oil phase. In a separate vessel the water phase ingredients are heated with mixing to 70°–75° C. Next, the oil phase is added to the water phase with mixing to form the emulsion. The mixture is then mixed while cooling to 40° C. In a separate vessel the phase C ingredients are combined and added to the emulsion with mixing. In another vessel the phase D ingredients are combined and added to the emulsion with mixing which is then cooled to room temperature. Next the Phase E ingredient (if any) and the Phase F ingredient are added with mixing.

The resulting lotion has enhanced substantivity (i.e. reisistance to water, perspiration, and rub-off), good stability, and is useful for topical application to the skin to provide an artificial tan and to provide protection from the harmful effects of ultraviolet radiation.

In alternative formulations the Polyquaternium 37 (and) Mineral Oil (and) PPG-1 Trideceth-6 is replaced with Polyquaternium 32 (and) Mineral Oil, available as Salcare$^R$ SC92 from Allied Colloids Ltd. (Norfolk, Va.).

Examples IV–VI

Artifical Tanning Creams Containing Sunscreens

| | % Weight | | |
|---|---|---|---|
| | IV | V | VI |
| Phase A | | | |
| Octyl Methoxycinnamate | 3.50 | 7.50 | 7.00 |
| Octocrylene | 1.00 | 3.75 | 7.50 |
| Benzophenone-3 | — | 2.00 | 4.20 |
| PVP Eicosene Copolymer | 2.00 | 2.00 | 2.00 |
| Glyceryl Tribehenate | 0.75 | 0.75 | 0.75 |
| Cetyl Palmitate | 0.75 | 0.75 | 0.75 |
| Polyquaternium 37 (and) Mineral Oil (and) PPG-1 Trideceth 6[1] | 1.75 | 1.50 | 1.25 |
| Isohexadecane | 1.00 | 1.00 | 2.00 |
| Cetyl Alcohol | 1.00 | 1.00 | 1.00 |
| Extracts of Aloe, Lanolin, Cocoa Butter, Palm, Chamomile, Eucalyptus, and Guava | 0.50 | — | — |
| Phase B | | | |
| Water | QS100 | QS100 | QS100 |
| Distearyl Dimethyl Ammonium Chloride | 0.20 | 0.20 | 0.20 |
| Hydroxyethylcellulose | 0.20 | 0.20 | 0.20 |
| Disodium EDTA | 0.05 | 0.05 | 0.05 |
| Phase C | | | |
| Water | 2.00 | 2.00 | 2.00 |
| Butylene Glycol | 2.00 | 2.00 | 2.00 |
| DMDM Hydantoin (and) Iodopropynyl Carbamate | 0.20 | 0.20 | 0.20 |
| Phase D | | | |
| Water | 6.00 | 6.00 | 6.00 |
| Dihydroxyacetone | 3.00 | 3.00 | 3.00 |
| Phase E | | | |
| Cyclomethicone | 2.00 | — | — |
| Phase F | | | |
| Fragrance | 1.00 | 0.50 | 0.50 |

[1]Available as Salcare$^R$ SC95 from Allied Colloids Ltd. (Norfolk, VA).

In a suitable vessel the phase A ingredients are combined and heated with mixing to 80°–85° C. to form an oil phase. In a separate vessel the water phase ingredients are heated with mixing to 70°–75° C. Next, the oil phase is added to the water phase with mixing to form the emulsion. The mixture is then mixed while cooling to 40° C. In a separate vessel the phase C ingredients are combined and added to the emulsion with mixing. In another vessel the phase D ingredients are combined and added to the emulsion with mixing which is then cooled to room temperature.

The resulting cream has enhanced substantivity (i.e. resistance to water, perspiration, and rub-off), good stability, and is useful for topical application to the skin to provide an artificial tan and to provide protection from the harmful effects of ultraviolet radiation.

In alternative formulations the Polyquaternium 37 (and) Mineral Oil (and) PPG-1 Trideceth-6 is replaced with Polyquaternium 32 (and) Mineral Oil, available as Salcare$^R$ SC92 from Allied Colloids Ltd. (Norfolk, Va.). Next the Phase E ingredient (if any) and the Phase F ingredient are added with mixing.

What is claimed is:

1. An oil-in-water emulsion composition useful for providing an artificial tan and UV protection comprising:

(a) from about 0.1% to about 20% dihydroxyacetone;

(b) from about 0.1% to about 30% of a sunscreen agent;

(c) from about 0.1% to about 10.0% of a crosslinked cationic polymer of the formula: $(A)_l(B)_m(C)_n$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is acrylamide, l is an integer of 0 or greater, m is an integer of 1 or greater, and n is an integer of 0 or greater, wherein said polymer contains a crosslinking agent selected from the group consisting of methlenebisacrylamides, diallyldialkyl ammonium halides, polyalkenyl polyethers of polyhydric alcohols, allyl acrylates, vinyloxyalkylacrylates, and polyfunctional vinylidenes;

(d) from about 0.1% to about 10% of a cationic emulsifier in the form of a quaternary ammonium salt having the formula:

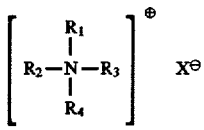

wherein $R_1$ is a $C_{12-22}$ alkyl group or $R_5CO—(CH_2)_n$— wherein $R_5$ is a $C_{12-22}$ alkyl group and n is an integer from about 2 to about 6, $R_2$ is H or a $C_{1-22}$ alkyl group, $R_3$ and $R_4$ are independently an H or a $C_{1-3}$ alkyl group, and X is an anion selected from the group consisting of chloride, bromide iodide, acetate, phosphate, nitrate, sulfate, methyl sulfate, ethyl sulfate, tosylate, lactate citrate, glycolate, and mixtures thereof;

(e) from about 30% to about 99.6% water, wherein said composition has a pH from about 2.5 to about 7.

2. The composition according to claim 1 wherein the crosslinking agent is selected from the group consisting of methylene bisacrylamide, ethylene glycol di-(meth)acrylate, di-(meth)acrylamide, cyanomethylacrylate, vinyloxyethyl acrylate, vinyloxyethylmethacrylate, allyl pentaerythritol, trimethylolpropane diallylether, allyl sucrose, butadiene, isoprene, divinyl benzene, divinyl naphthalene, allyl acrylate, and mixtures thereof.

3. The composition according to claim 2 wherein said crosslinking agent is methylene bisacrylamide.

4. The composition according to claim 3 wherein the amount of (C) in the cationic polymer is from about 50% to about 90% molar.

5. The composition according to claim 3 wherein l in the cationic polymer is zero and the ratio of (B):(C) is from about 45:55 to about 55:45.

6. The composition according to claim 3 wherein both l and n are zero in the cationic polymer.

7. The composition according to claim 1 wherein said cationic polymer comprises from about 0.1% to about 5%.

8. The composition according to claim 7 wherein said cationic polymer comprises from about 0.5% to about 2%.

9. The composition according to claim 8 wherein said cationic polymer is selected from the group consisting of Polyquaternium 32, Polyquaternium 37, and mixtures thereof.

10. The composition according to claim 9 wherein said cationic emulsifier is selected from the group consisting of dilauryl dimethyl ammoniun chloride, distearyl dimethyl ammonium chloride, dimyristyl dimethyl ammonium chloride, dipalmityl dimethyl ammonium chloride, distearyl dimethyl ammonium chloride, and mixtures thereof.

11. The composition according to claim 10 wherein said dihydroxyacetone comprises from about 2% to about 7%.

12. The composition according to claim 11 wherein said dihydroxyacetone comprises from about 3% to about 5%.

13. The composition according to claim 12 wherein said pH is from about 2.5 to about 6.

14. The composition according to claim 13 wherein said pH is from about about 3.5 to about 5.

15. The composition according to claim 14 wherein said sunscreen agent comprises from about 0.5% to about 25%.

16. The composition according to claim 15 wherein said sunscreen agent comprises from about 1% to about 20%.

17. The composition according to claim 16 wherein said sunscreen agent is selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, titanium dioxide, zinc oxide, iron oxide, and mixtures thereof.

18. The composition according to claim 17 which further comprises from about 0.1% to about 2% of a fatty alcohol.

19. The composition according to claim 18 wherein said fatty alcohol is selected from the group consisting of lauryl alcohol, myristyl alcohol, palmityl alcohol, stearyl alcohol, isostearic alcohol, oleyl alcohl, linoleyl alcohol, linolenyl alcohol, ricinoleyl alcohol, behenyl alcohol, and mixtures thereof.

20. The composition according to claim 19 which further comprises from about 1% to about 5% of a humectant selected from the group consisting of glycerin, butylene glycol, hexylene glycol and mixtures thereof.

21. The composition according to claim 20 which further comprises from about 1% to about 10% of an emollient selected from the group consisting of volatile silicone oils, non-volatile silicone oils, highly branched hydrocarbons, and mixtures thereof.

22. A method for providing both an artificial tan to human skin and protecting human skin from the effects of ultraviolet radiation, said method comprising topically applying to the skin an effective amount of a composition according to claim 1.

* * * * *